United States Patent [19]

Takayama

[11] 4,281,910
[45] Aug. 4, 1981

[54] CAMERA APPARATUS FOR ENDOSCOPE

[75] Inventor: Syuichi Takayama, Hachioji, Japan

[73] Assignee: Olympus Optical Co., Ltd., Japan

[21] Appl. No.: 127,515

[22] Filed: Mar. 5, 1980

[30] Foreign Application Priority Data

Apr. 2, 1979 [JP] Japan .................................. 54/39610

[51] Int. Cl.³ .......................... G03B 29/00; A61B 1/04
[52] U.S. Cl. ......................................... 354/62; 354/63;
354/79; 350/19; 128/4
[58] Field of Search ............... 354/62, 63, 79; 350/19;
128/4, 5, 6, 7, 8, 9

[56] References Cited

U.S. PATENT DOCUMENTS

| | | | |
|---|---|---|---|
| 3,987,463 | 10/1976 | Nishikawa et al. | 354/79 |
| 4,145,130 | 3/1979 | Shimizu et al. | 354/51 |
| 4,153,356 | 5/1979 | Hama | 354/62 |
| 4,168,702 | 9/1979 | Ohshiro | 354/62 |
| 4,192,597 | 3/1980 | Ting | 354/62 |

Primary Examiner—Russell E. Adams
Attorney, Agent, or Firm—Ostrolenk, Faber, Gerb & Soffen

[57] ABSTRACT

A camera apparatus can be mounted on an endoscope to enable a picture to be taken of the interior of a coeliac cavity. The apparatus comprises a detecting device which detects whether the apparatus is or is not mounted on an endoscope. When the apparatus is mounted, the detecting device operates to supply power to an electrical circuit of the apparatus which requires energization only during a photographing operation, which power may be drawn from either an internal battery or an external power supply, thus minimizing the power dissipation of the internal battery.

7 Claims, 13 Drawing Figures

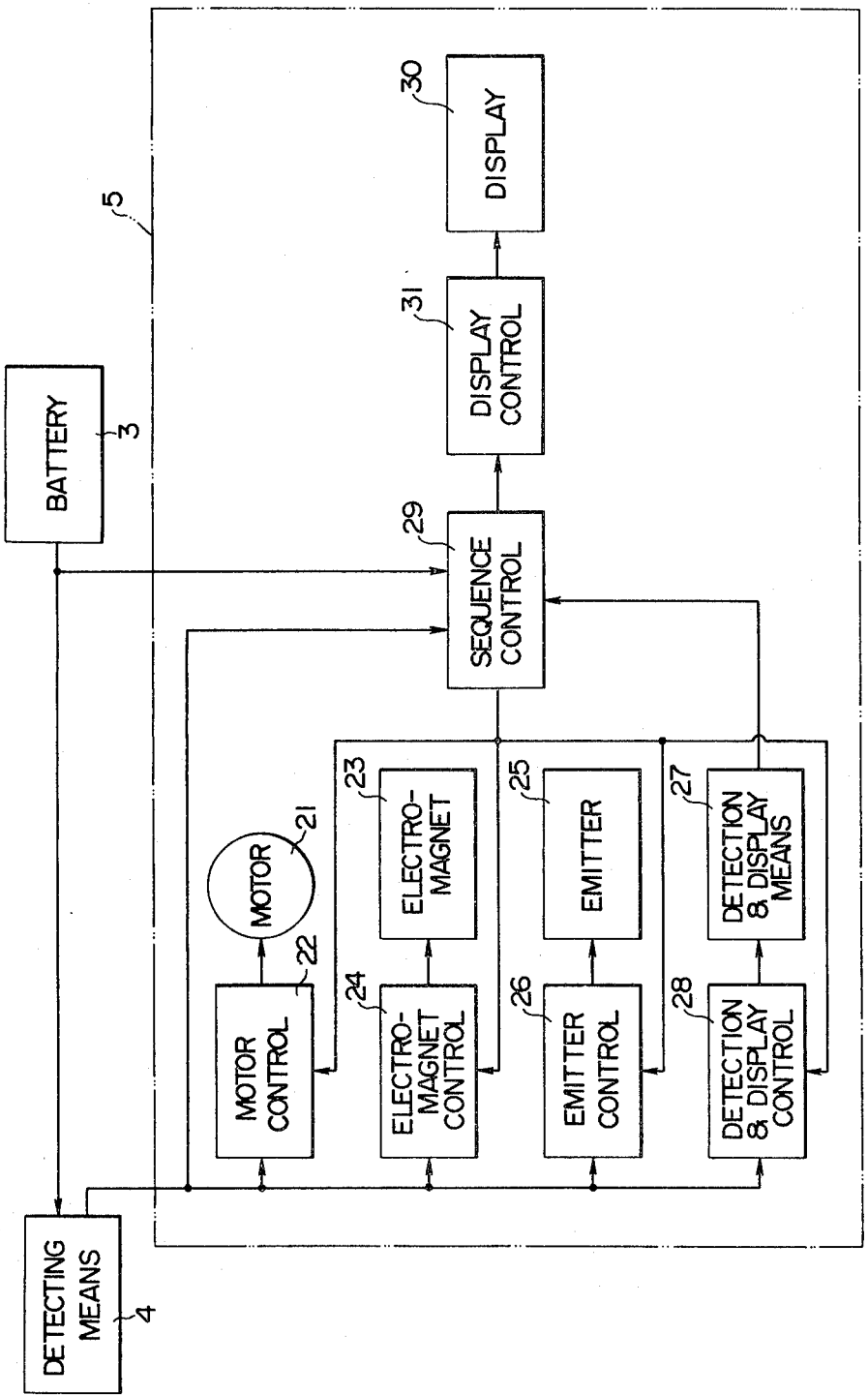

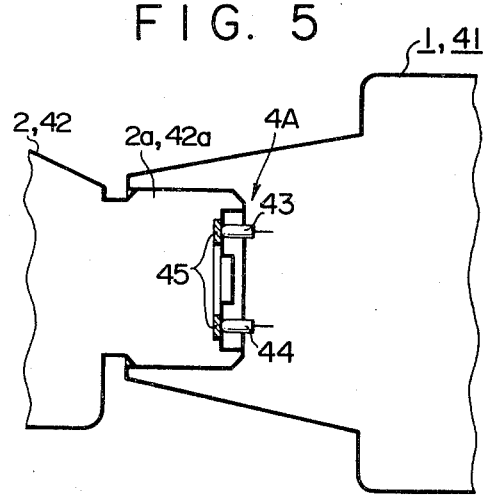
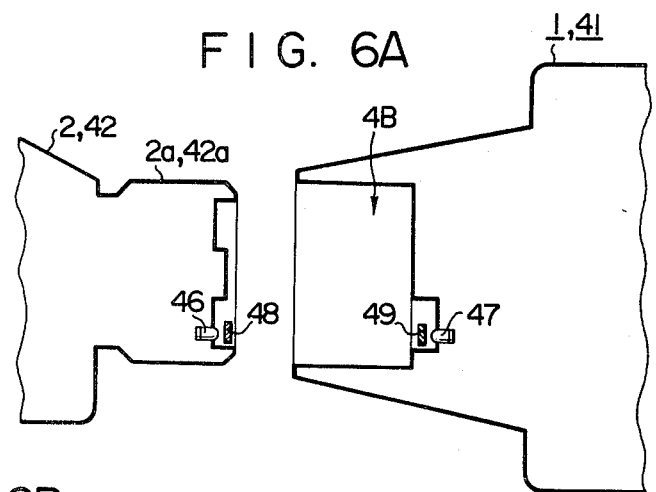
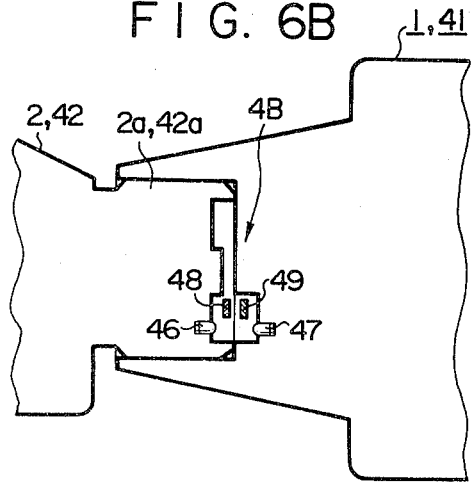

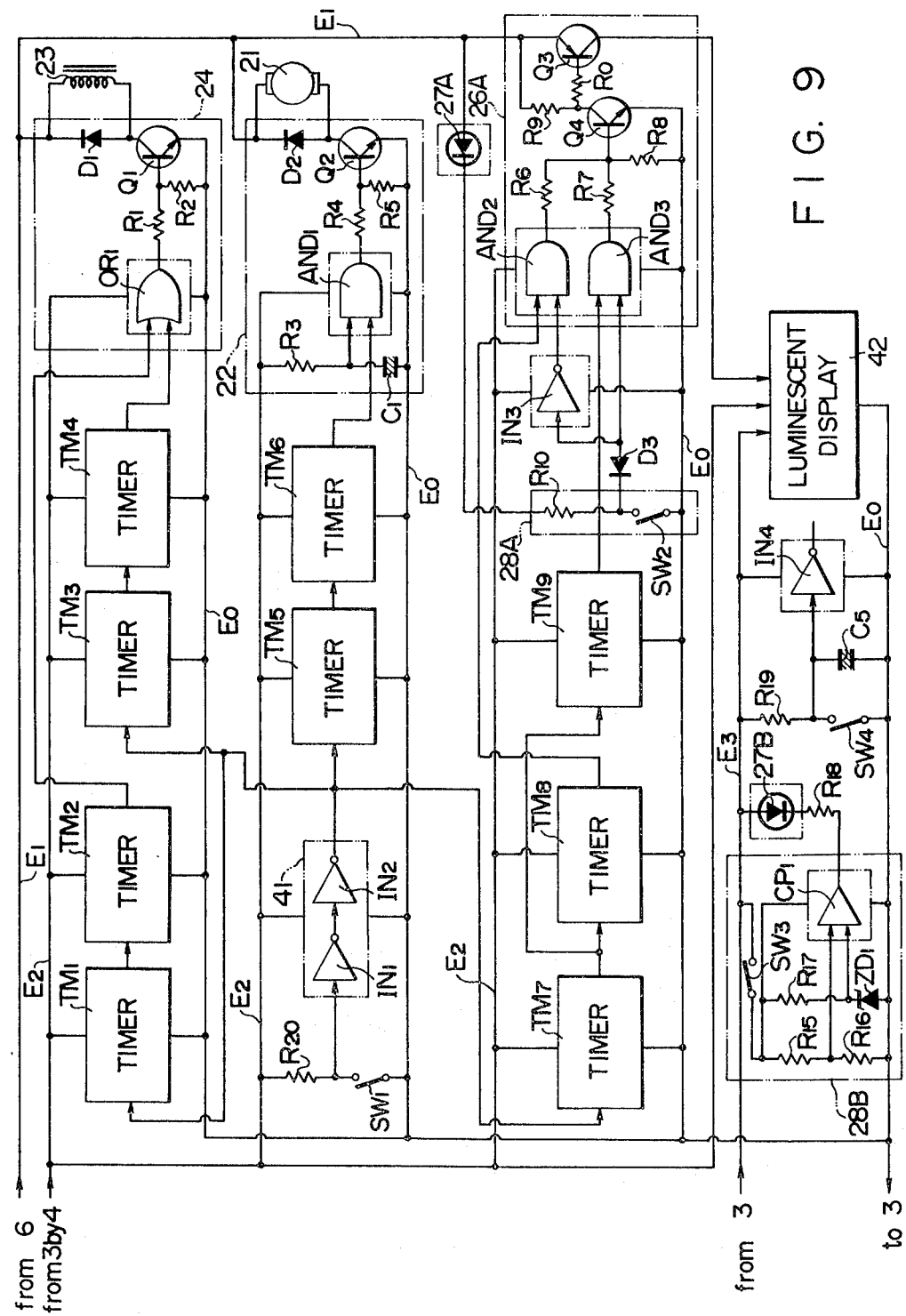
F I G. 9

CAMERA APPARATUS FOR ENDOSCOPE

BACKGROUND OF THE INVENTION

The invention relates to a camera apparatus for an endoscope, and more particularly, to a camera apparatus detachably mounted on an endoscope and having its various functions associated with photographing operations to be electrically driven and controlled.

As is well known, cameras manufactured for use with an endoscope are adapted to be mounted on an endoscope to take a picture of the interior of a coeliac cavity. A camera of this kind is known in which a series of functions including a shutter release and a film winding associated with a photographing operation are electrically driven and controlled. A camera which is electrically driven and controlled in this manner contains a variety of electrical components and electrical circuits, which can be categorized in a manner described below, depending on the magnitude of their power dissipation and the timing when they require a power supply.

1. Electrical components having an increased power dissipation and which need be supplied with power only during a photographing operation:
    (a) an electric motor which effects a film winding as well as a charging operation for operating a mirror shutter release;
    (b) an electromagnet which controls the operation of the mirror shutter;
    (c) light emitting assembly comprising a combination of segment-shaped elements such as photodiodes and which is utilized to enter various data such as picture number, date, time of day and the number of film frames onto a film; and
    (d) detection and display means formed by light emitting diodes or the like for detecting and displaying the film speed and the voltage of an internally housed battery;

2. Electrical circuits which exhibit a reduced power dissipation and which need be supplied with power only during a photographing operation:
    (a) a control circuit associated with the motor;
    (b) a control circuit associated with the electromagnet;
    (c) a control circuit associated with the light emitting assembly; and
    (d) a control circuit associated with the detection and display means;

3. Electrical components and circuits which must be normally supplied with power:
    (a) a sequence control circuit for controlling the sequence of operation of the motor control circuit, the electromagnet control circuit, the light emitting assembly control circuit, the detection and display means control circuit, and a display control circuit to be described later;
    (b) a display formed by a combination of segment-shaped elements such as liquid crystal elements for providing a display, externally of the camera apparatus, of various data including picture number, date, time of day and the number of film frames; and
    (c) a control circuit associated with the display and including a clock circuit which must be maintained in operation to provide a display of the date and the time of day and a storage circuit for storing the number of film frames.

In order to reduce the power dissipation of a battery which is internally housed within the camera, and thereby increase the useful life of the battery prior art cameras of the type described above supply power to the components and circuits mentioned under the item 3 which normally require energization, from the internal battery while supplying other components and circuits from an external power source such as the source provided within a light source device of an endoscope used only during a photographing operation. Alternatively, those components and circuits which do not require energization at all times are supplied from the internal battery only during a photographing operation.

The components and circuits mentioned under items 1 and 2 which require a power supply only during a photographing operation may be fed by connection with an external source at the desired times. By way of example, an energization of the electrical circuits of the camera apparatus may be started in response to the depression of a shutter release button (see U.S. Pat. No. 4,145,130) or in response to a movement of a film winding lever from its inoperative to its operative position. However, with these known approaches, the energization cannot be started unless a photographing operation is initiated. Consequently, it is impossible to provide an idle, automatic film winding by means of an internally housed motor or to provide a film winding in order to prevent fogging. Even if possible, the resulting operation will be a very troublesome one.

SUMMARY OF THE INVENTION

It is an object of the invention to provide a camera apparatus for an endoscope which detects that the camera apparatus is mounted on an endoscope to initiate the energization of electrical circuits contained therein which require energization during a photographing operation, from an internally housed battery or an external power source, thus minimizing the power dissipation of the internal battery.

In accordance with the invention, there is provided a camera apparatus for an endoscope including a first electrical circuit which must be normally energized, a second electrical circuit which must be energized during a photographing operation, and an internally housed battery which feeds at least the first electrical circuit wherein means is provided to detect that the camera apparatus is or is not mounted on an endoscope, the detecting means being operative to cause the second electrical circuit to be fed from the internal battery or an external power source.

In this manner, the first electrical circuit which must be normally energized is normally fed in accordance with the invention, thus maintaining its functioning. At the same time, the second electrical circuit which requires its energization during a photographing operation begins to be fed in response to a mounting of the camera apparatus on an endoscope. In this manner, the power dissipation of the internal battery is minimized.

However, when the camera apparatus is mounted on the endoscope, all the electrical circuits of the camera apparatus are energized, and hence the camera apparatus can exercise its full capability, enabling an idle, film winding or a film winding to prevent fogging to be simply performed.

BRIEF DESCRIPTION OF THE DRAWINGS

FIG. 4 is a block diagram of an electrical control device which is disposed in the camera apparatus of FIG. 3;

FIGS. 5, 6A and 6B are schematic views of detecting means used with the camera apparatus shown in FIGS. 1, 2 and 3 and 4, respectively;

FIG. 9 is a circuit diagram of a specific example of the electrical control device shown in FIG. 2;

DESCRIPTION OF PREFERRED EMBODIMENTS

Figure 1:
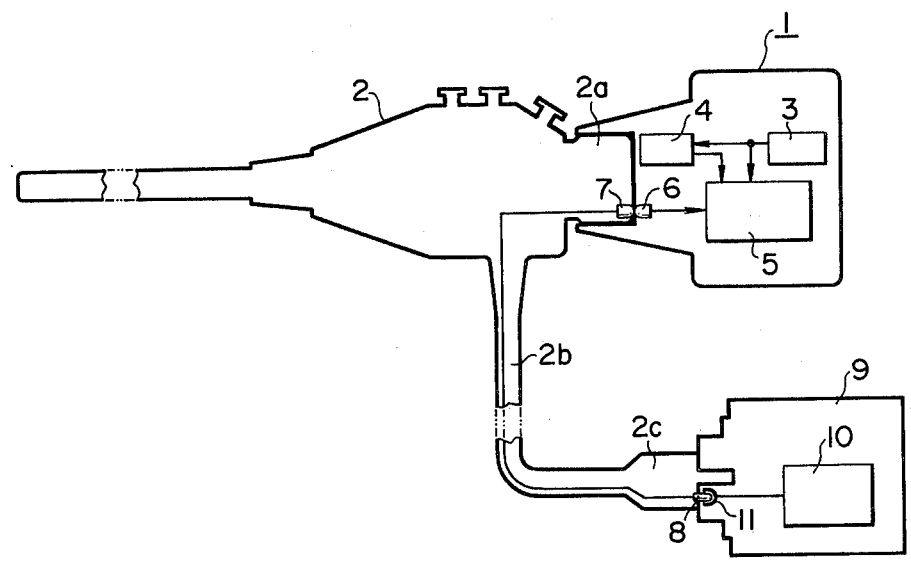
FIG. 1 is a schematic view showing the general arrangement of a camera apparatus for an endoscope according to one embodiment of the invention.

Referring to FIG. 1, there is shown a camera apparatus 1 for an endoscope according to one embodiment of the invention, which is illustrated as mounted on an eyepiece assembly 2a of an endoscope 2. The camera apparatus 1 internally houses detecting means 4 which detects that the apparatus 1 is mounted on the endoscope 2, an electrical control device 5 which includes the essential parts of a control mechanism for the camera apparatus 1, and a connection terminal 6 for connection with an external power source. The terminal 6 is located so as to mate with a supply output terminal 7 which is disposed on the part of the eyepiece assembly 2a of the endoscope, so that when the camera apparatus 1 is mounted on the eyepiece assembly 2a, both terminals 6, 7 mate with each other to establish an electrical interconnection. The output terminal 7 is connected through a light source connection tube 2b of the endoscope 2 with a supply terminal 8 which is provided on the part of a connector assembly 2c, which is in turn adapted to be connected with a feed terminal 11 electrically connected to a power supply 10 of a light source unit 9 whenever the connector assembly 2c is connected to the light source unit 9. In this manner, when the camera apparatus 1 is mounted on the endoscope 2, it is fed from the power supply 10 of the light source unit 9, in addition to the internally housed battery 3.

Figure 2:
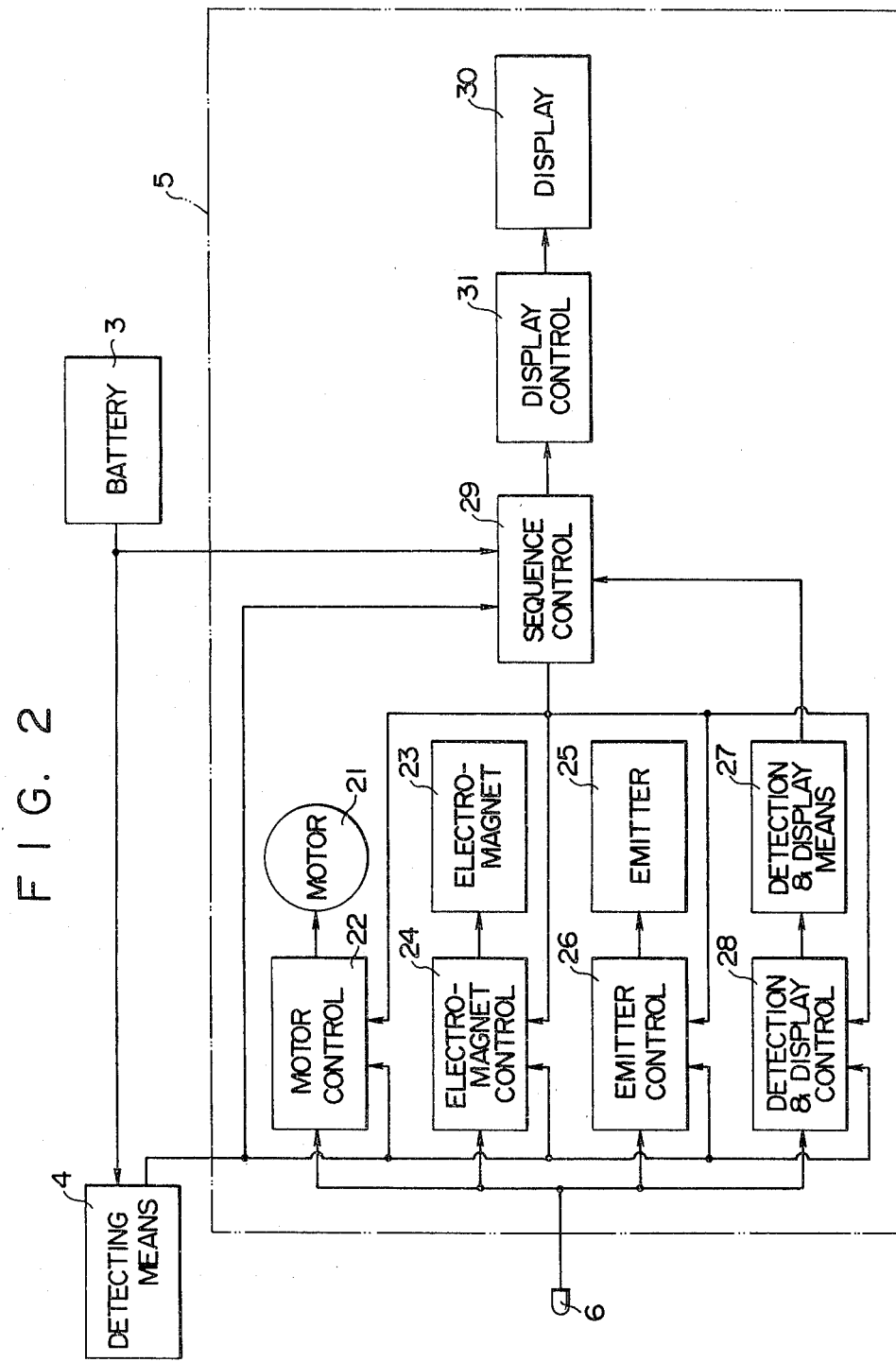
FIG. 2 is a block diagram of an electrical control device which is disposed in the camera apparatus of FIG. 1.

Referring to FIG. 2, which shows the electrical control device 5 in more detail, it essentially comprises a film winding motor 21, a motor control circuit 22, a shutter release electromagnet 23, a control circuit 24 associated with the electromagnet 23, a data entry light emitting assembly 25, a control circuit 26 associated with the light emitting assembly 25 and formed by a decoder, a driver and the like, detection and display means 27 which includes a film speed sensor and a battery checker associated with the battery 3, a control circuit 28 associated with the detection and display means 27, a sequence control circuit 29, a display 30 which is used to provide an external indication of the number of film frames and the date when a picture is taken, and a control circuit 31 associated with the display and formed by a decoder, a driver and the like.

The battery 3 is connected to a number of components including detecting means 4 and the sequence control circuit 29 directly, to the motor control circuit 22, the electromagnet control circuit 24, the light emitting assembly control circuit 26, the control circuit 28 associated with the detection and display means and the sequence control circuit 29 through the detecting means 4, and also connected through a series combination of the sequence control circuit 29 and its connected display control circuit 31 to the display 30. The sequence control circuit 29 is connected to the motor control circuit 22, the electromagnet control circuit 24, the light emitting assembly control circuit 26 and the control circuit 28 associated with the detection and display means, respectively. The connection terminal 6 is connected to the motor 21, the electromagnet 23, the light emitting assembly 25 and the detection and display means 27 through their respective control circuits 22, 24, 26, 28, respectively. The detection and display means 27 is also connected to the sequence control circuit 29.

In operation, when the camera apparatus 1 is not mounted on the endoscope 2, the battery 3 is connected to only the display 30 and the display control circuit 31 through the sequence control circuit 29. The display 30 provides a display of the number of film frames and the date in accordance with an output from the display control circuit 31.

When the camera apparatus 1 is mounted on the endoscope 2, the detecting means 4 detects that it is mounted, and effects a switching operation to connect the battery 3 to other control circuits 22, 24, 26 and 28. In addition, the detecting means 4 produces a signal indicative of the fact that the camera apparatus 1 is mounted on the endoscope 2, which signal is applied to the sequence control circuit 29. As the control circuits 22, 24, 26 and 28 are activated, the power from the power supply 10 (see FIG. 1) which is now supplied through the connection terminal 6 is fed to the motor 21, the electromagnet 23, the light emitting assembly 25 and the detection and display means 27 at the same time as the camera apparatus 1 is mounted on the endoscope 2. As a consequence, in response to a photographing operation such as the depression of a shutter release button, not shown, the sequence control circuit 29 controls the individual control circuits 22, 24, 26 and 28, causing a film winding operation by the motor 21, or causing the electromagnet 23 to effect a shutter release operation.

Figure 3:
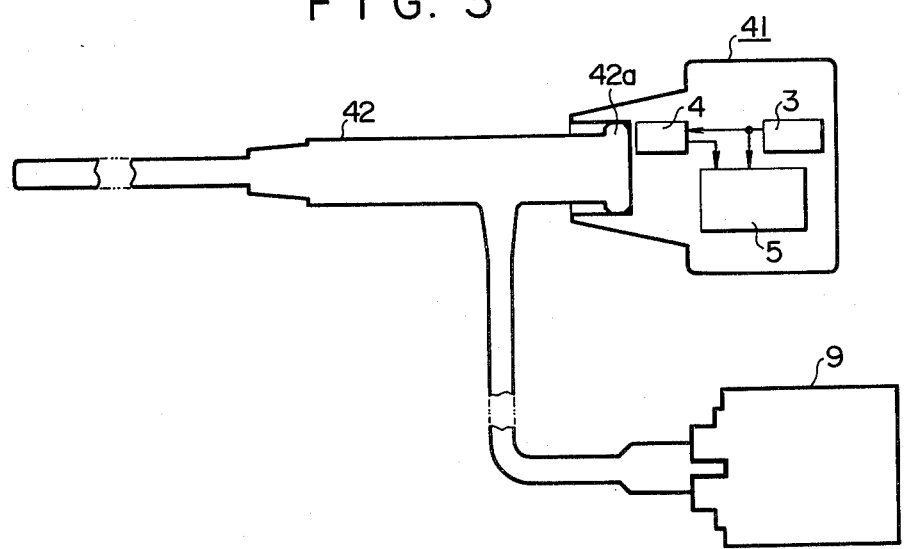
FIG. 3 is a schematic view of a camera apparatus for an endoscope according to another embodiment of the invention.

FIGS. 3 and 4 show the general arrangement and an electrical circuit of a camera apparatus for endoscope which is constructed according to another embodiment of the invention. As shown, a camera apparatus 41 is adapted to be mounted on an endoscope 42 of hard type, the eyepiece assembly 42a of which is not provided with a power terminal. Thus the camera apparatus 41 is essentially the same as that shown in FIGS. 1 and 2 except that connection terminals for connection with an external power supply are not provided. Hence, corresponding parts are designated by like reference numerals without repeating their description.

The apparatus 41 operates in quite the same manner as the camera apparatus 1 except that the motor 21, the electromagnet 23, the light emitting assembly 25 and the detection and display means 27 are fed from the internal battery 3.

FIG. 5 shows a specific example of detecting means 4 which may be preferably used in the camera apparatus 1 or 41 shown in FIGS. 1 to 4. The detecting means 4A comprises a detecting terminal 43 connected to the battery 3 (see FIGS. 1 and 3) and a detecting terminal 44 connected to the sequence control circuit 29 and the individual control circuits 22, 24, 26 and 28 (see FIGS. 2 and 4), both of which are disposed in that portion of the camera apparatus 1 or 41 which is adapted to mate with the eyepiece assembly of the endoscope. When the camera apparatus 1 or 41 is mounted on the endoscope 2 or 42, both detecting terminals 43, 44 of the detecting means 4A are short-circuited by an electrically conductive member 45 which is disposed on the eyepiece assembly 2a and 42a of the endoscope to feed the individual control circuits 22, 24, 26 and 28 from the battery 3. The detecting means 4A also transmits a mounting detected signal to the sequence control circuit 29.

FIGS. 6A and 6B show another form of detecting means 4B. Detecting means 4B comprises a light emitting element 46 such as a light emitting diode which is disposed in the eyepiece assembly 2a or 42a of the endoscope 2 or 42 in combination with a light receiving element 47 such as a photodiode or phototransistor which is disposed in the mating portion of the camera apparatus 1 or 41. In this manner, it provides a photoelectric detection of the mounting of the camera apparatus 1 or 41 onto the endoscope 2 or 42. More specifically, in addition to the elements 46 and 47, the detecting means 4B includes a light shield member 48 which is disposed forwardly of the light emitting element 46 on the endoscope, preventing an external leakage of light therefrom when the camera apparatus 1 is not mounted on the endoscope, and another light shield member 49 disposed forwardly of the light receiving element 47 in order to prevent the element 47 from operating in response to an extraneous light such as natural light when the apparatus is not mounted on the endoscope 2 or 42. It will be noted from FIG. 6B that the light shield members 48, 49 retract from their positions located forwardly of the elements 46, 47 whenever the camera apparatus 1 or 41 is mounted on the endoscope 2 or 42 to leave the elements 46, 47 in opposing relationship.

Because no electrical contact is used, the detecting means 4B affords the advantage that a more stable operation is achieved as compared with detecting means 4A, free from the problem of poor contact between or the formation of rust on terminals and conductive members.

Figure 7:
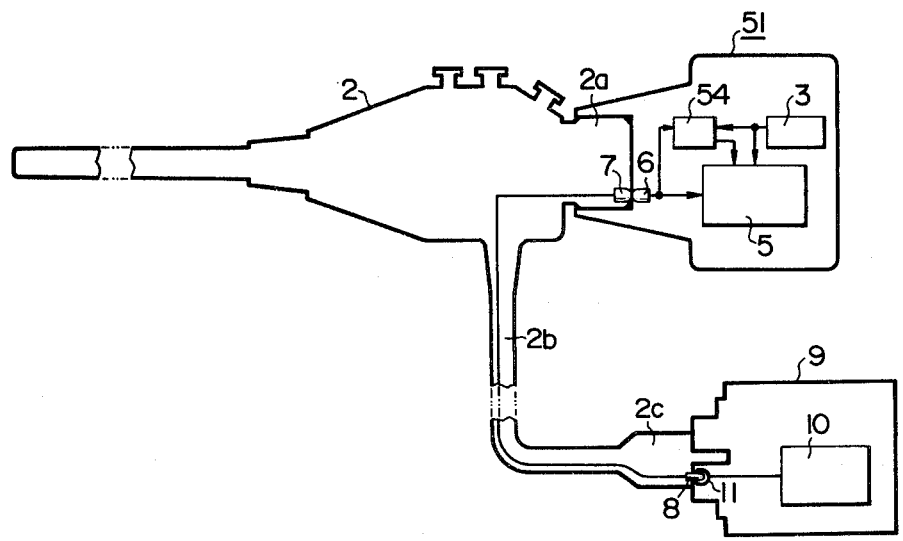
FIG. 7 is a schematic view of a camera apparatus for an endoscope according to a further embodiment of the invention.
Figure 8:
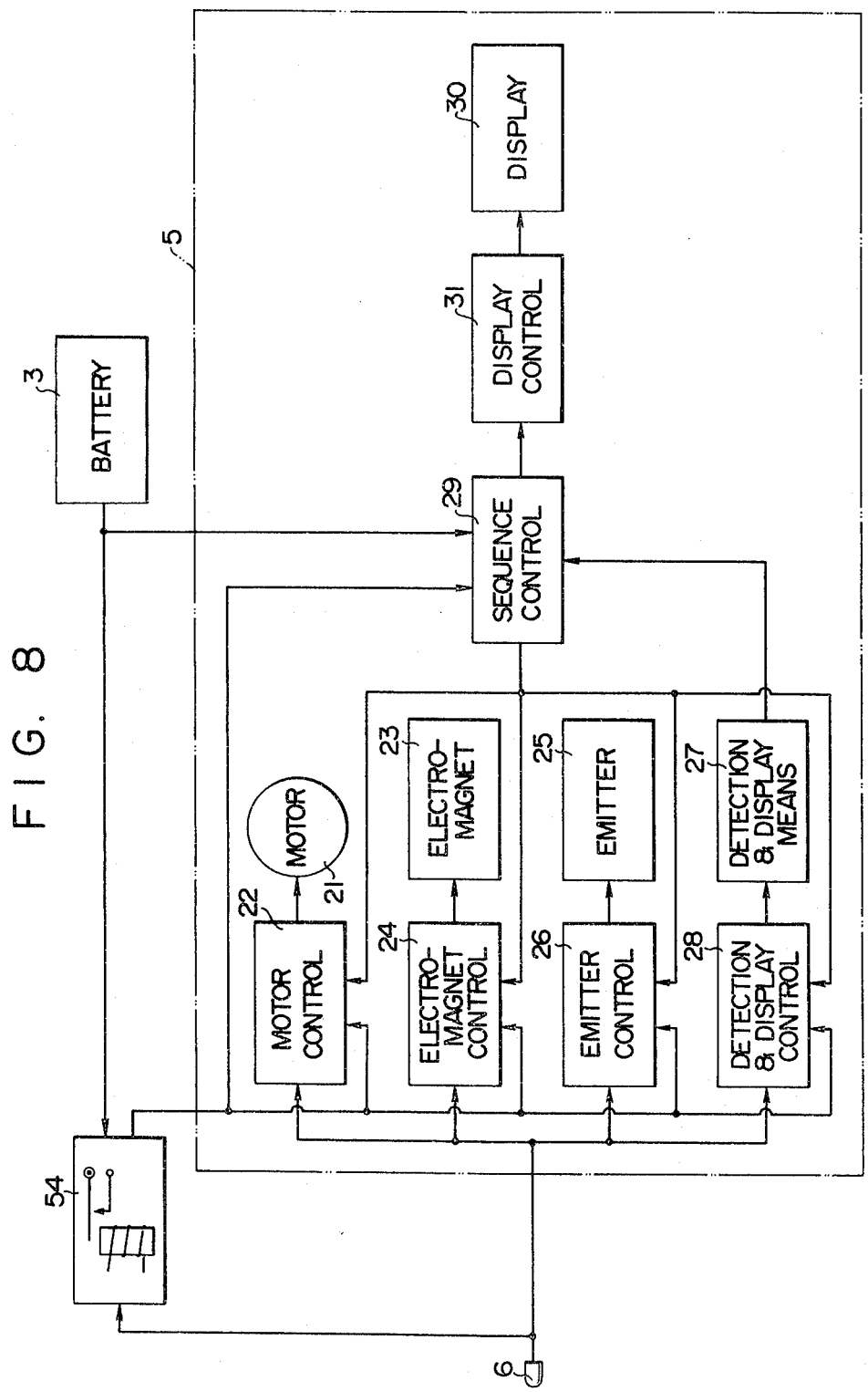
FIG. 8 is a block diagram of an electrical control device which is disposed in the camera apparatus of FIG. 7.

FIGS. 7 and 8 show a camera apparatus for an endoscope according to a further embodiment of the invention. The camera apparatus 51 is a modification of the camera apparatus 1 shown in FIGS. 1 and 2 in that the direct detection of a mounting of the apparatus onto the endoscope 2 by detecting means 4 is replaced by a switch circuit formed by a relay circuit which is operated by power from the external power supply 10 which is fed through the connection terminal 6 whenever the apparatus is mounted on the endoscope 2. Consequently, the camera apparatus 51 is similar to the camera apparatus 1 in that the detecting means 4 is replaced by a switch circuit 54 which is connected to the connection terminal 6. Other parts are designated by like reference characters, and hence will not be described. It should be understood that the switch circuit 54 may be formed by a semiconductor switching element. It will be appreciated that the camera apparatus 51 functions in the same manner as the camera apparatus 1 of FIGS. 1 and 2.

FIG. 9 shows a specific electric circuit of the electrical control device shown in FIG. 2. In the electrical circuit shown, the electromagnet control circuit 24 comprises OR circuit $OR_1$, switching transistor $Q_1$, a pair of resistors $R_1$, $R_2$ and diode $D_1$. The transistor $Q_1$ comprises an NPN transistor having its collector connected through the electromagnet 23 to a supply bus $E_1$ which is in turn connected to the connection terminal 6, its emitter connected to a common ground line $E_0$ connected to a ground terminal which is not shown in FIG. 2, and its base connected through resistor $R_1$ to the output of OR circuit $OR_1$, respectively. A bias resistor $R_2$ is connected across the base and emitter of the transistor $Q_1$. The electromagnet 23 is shunted by diode $D_1$, which serves to suppress a counter electromotive force developed across the electromagnet 23 as the latter is deenergized. OR circuit $OR_1$ is connected between a supply bus $E_2$ and the ground line $E_0$. The bus $E_2$ is adapted to feed an operating voltage during a photographing operation, and is connected to the battery 3 through the detecting means 4. OR circuit has its one input connected to the output of timer circuit $TM_2$ which controls the duration during which the electromagnet 23 remains energized to allow a mirror shutter, not shown, disposed within the camera apparatus 1 out of a taking light path. The other input of OR circuit is connected to the output of timer circuit $TM_4$ which controls the duration during which the electromagnet 23 is energized to allow the mirror shutter to move down into the taking light path. Timer circuit $TM_2$ has its input connected to the output of timer circuit $TM_1$ which controls the timing when the energization of the electromagnet 23 is initiated to thereby allow the mirror shutter to move up. Timer circuit $TM_4$ has its input connected to the output of timer circuit $TM_3$ which controls the timing when the electromagnet 23 is energized in order to allow the mirror shutter to move down. Both timer circuits $TM_1$ and $TM_3$ have their input connected in common to one end of a shutter release switch $SW_1$ through a waveform shaping buffer circuit 41, to be described later.

The motor control circuit 22 comprises AND circuit $AND_1$, switching transistor $Q_2$, three resistors $R_3$–$R_5$, noise suppressing capacitor $C_1$ and diode $D_2$. The transistor $Q_2$ comprises an NPN transistor having its collector connected to the supply bus $E_1$ through the motor 21, its emitter to the ground lines $E_0$ and its base to the output of AND circuit $AND_1$ through resistor $R_4$. A bias resistor $R_5$ is connected across the base and emitter of the transistor $Q_2$. The diode $D_2$ serves suppressing a counter electromotive force developed upon interruption of the energization of the motor 21, and hence is connected in shunt therewith. AND circuit $AND_1$ is connected across the bus $E_2$ and the ground line $E_0$, and has its one input connected to the junction between resistor $R_3$ and capacitor $C_1$ which are connected in series across the buses $E_2$, $E_0$. As mentioned previously, the purpose of capacitor $C_1$ is to suppress noises, and it also prevents a malfunctioning of the motor 21 when the power is initially turned on. When the bus $E_2$ is connected to the battery 3, the capacitor maintains an "L" level at one input of AND circuit $AND_1$ for a given time interval, and supplies an "H" level at the same input terminal subsequently, thus preventing the input from inadvertently assuming an "L" level. The other input of AND circuit $AND_1$ is connected to the output of timer circuit $TM_6$ which controls the duration during which the motor 21 is driven in order to wind up a film. The input of timer circuit $TM_6$ is connected to the output of timer circuit $TM_5$ which controls the timing when the motor 21 begins to be driven. The input of timer circuit $TM_5$ is connected to one end of shutter release switch $SW_1$ through the waveform shaping buffer circuit 41.

The light emitting assembly control circuit 26 comprises a switching circuit 26A which turns on or off the power supply to the light emitting assembly 25, a decoder driver circuit 26B (see FIG. 10) for driving a pair of light emitting elements 25a, 26b used for the entry of the number of film frames, and a buffer circuit 26C (see FIG. 10) for driving four light emitting elements 25c–25f for the entry of the date when a picture is taken. The switching circuit 26A comprises a pair of AND circuits $AND_2$, $AND_3$, a pair of transistors $Q_3$, $Q_4$ and four resistors $R_6$–$R_9$. The transistors $Q_3$, $Q_4$ comprise an NPN and a PNP transistor. The transistor $Q_3$ has its emitter connected to the bus $E_1$, its collector connected to individual light emitting elements 25a–25f (see FIG. 10) which are disposed in a luminescent display 42, and its base to the collector of the other transistor $Q_4$ through resistor $R_0$. Resistor $R_9$ is connected between the collector of the transistor $Q_4$ and the emitter of the transistor $Q_3$. The transistor $Q_4$ has its emitter connected to the ground line $E_0$ and its base connected through resistor $R_6$ to the output of AND circuit $AND_2$ and also connected through resistor $R_7$ to the output of the other AND circuit $AND_3$. A bias resistor $R_8$ is connected across the base and emitter of the transistor $Q_4$. AND circuit $AND_2$ has its one input connected to the output of timer circuit $TM_8$ which causes the light emitting elements 25 (25a–25f) to emit light for an increased length of time, and has its other input connected to one end of a film speed establishing switch $SW_2$ through a combination of polarity inverting inverter $IN_3$ and diode $D_3$. AND circuit $AND_3$ has its one input connected to the output of timer circuit $TM_9$ which causes the light emitting assembly 25 to emit light for a reduced length of time, and its other input connected through diodes $D_3$ to one end of the film speed establishing switch $SW_2$. Timer circuits $TM_8$ and $TM_9$ have their input connected in common to the output of timer circuit $TM_7$ which controls the timing when the light emitting assembly 25 begins to emit light. The input of timer circuit $TM_7$ is connected to one end of shutter release switch $SW_1$ through the waveform shaping buffer circuit 41. The film speed establishing switch $SW_2$ has its other end connected to the ground line $E_0$ while one end is connected through resistor $R_{10}$ to the cathode of light emitting diode 27A which operates as a film speed detection and display means. The combination of the switch $SW_2$ and resistor $R_{10}$ constitutes a control circuit 28A for the light emitting diode 27A, which has its anode connected to the bus $E_1$. Whenver the bus $E_1$ is connected to the external power supply 10 and the switch $SW_2$ is closed, the light emitting diode 27A is illuminated to provide an indication externally of the camera apparatus 1 that the film used is of a low speed. The fact that the light emitting diode 27A is not illuminated indicates that the film used is of a high speed. It is to be noted that the film speed establishing switch $SW_2$ is automatically operated in response to the detection of a film speed indicating mark on the film used. The inverter $IN_3$ has its input connected to the anode of diode $D_3$ and functions to invert a switch $SW_2$ signal that is fed to the other input of AND circuit $AND_3$ before it is supplied to the other input of AND circuit $AND_2$. This prevents AND circuits $AND_2$ and $AND_3$ from being enabled simultaneously, selecting either a long or a short duration during which the light emitting assembly 25 emits light for purpose of data entry.

The buffer circuit 41 which has its output connected to the input of timer circuits $TM_1$, $TM_3$, $TM_5$ and $TM_7$ comprises a series combination of a pair of inverters $IN_1$ and $IN_2$ which is connected across the buses $E_2$ and $E_0$. The input of the buffer circuit 41 is connected to the junction between the shutter release switch $SW_1$ and resistor $R_{20}$ connected in series across the buses $E_2$, $E_0$, thus effecting a waveform shaping, by the double inversion, of the switch $SW_1$ close signal which occurs as a shutter release button (not shown) is depressed.

Figure 11:
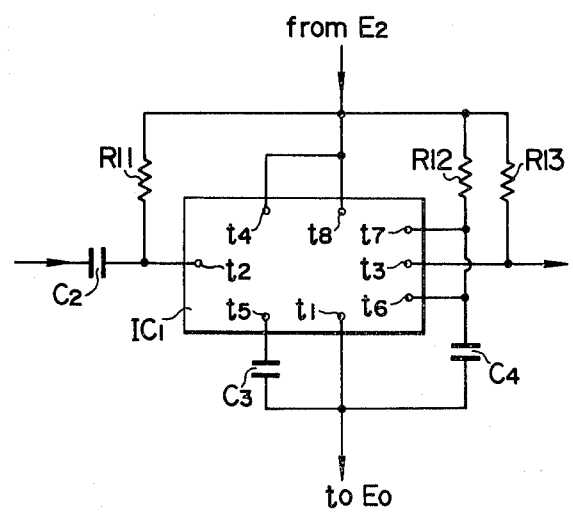
FIG. 11 is a circuit diagram of a timer circuit shown in FIG. 9.

Timer circuit $TM_1$ to $TM_9$ have an identical circuit arrangement, which is illustrated in FIG. 11. As shown, it comprises a time delay producing, integrated circuit $IC_1$ (for example, HA17555 manufactured by Hitachi Mfg., Co. or NE555 manufactured by Signestics, Inc.), three capacitors $C_2$–$C_4$ and three resistors $R_{11}$–$R_{13}$, all of which constitute together a monostable multivibrator. Integrated circuit $IC_1$ has eight terminals $t_1$–$t_8$ including a ground (GND), trigger, output, reset, control voltage, threshold, discharge and supply (Vcc) terminal. Trigger terminal $t_2$ is connected with one end of a differentiating capacitor $C_2$ which has its other end connected to the input of timer circuits $TM_1$–$TM_9$. The trigger terminal $t_2$ is also connected with supply bus $E_2$ through a resistor $R_{11}$ which forms a differentiator together with capacitor $C_2$. Output terminal $t_3$ represents the output terminal of timer circuits $TM_1$–$TM_9$ for connection with a succeeding circuit. Output terminal $t_3$ is also connected to ground line $E_2$ through resistor $R_{13}$. Reset terminal $t_4$ is connected to ground line $E_2$ together with supply terminal $t_8$. Control voltage terminal $t_5$ is connected to the ground line $E_0$ through a stabilizing capacitor $C_3$. Threshold terminal $t_6$ is connected to the line $E_0$ through a timing capacitor $C_4$ while discharge terminal $t_7$ is connected to the line $E_2$ through a timing resistor $R_{10}$. It will be noted that the both terminals $t_6$ and $t_7$ are connected to each other. Ground terminal $t_1$ is connected to the ground line $E_0$. In response to a negative trigger pulse applied to the trigger terminal $t_2$, each of timer circuits $TM_1$ to $TM_9$ produces an output of "H" level, whereby capacitor $C_4$ is charged with a time constant determined by its combination with resistor $R_{12}$. When the voltage across capacitor $C_4$ reaches the threshold voltage, it discharges, returning the output to "L" level.

Figure 12:
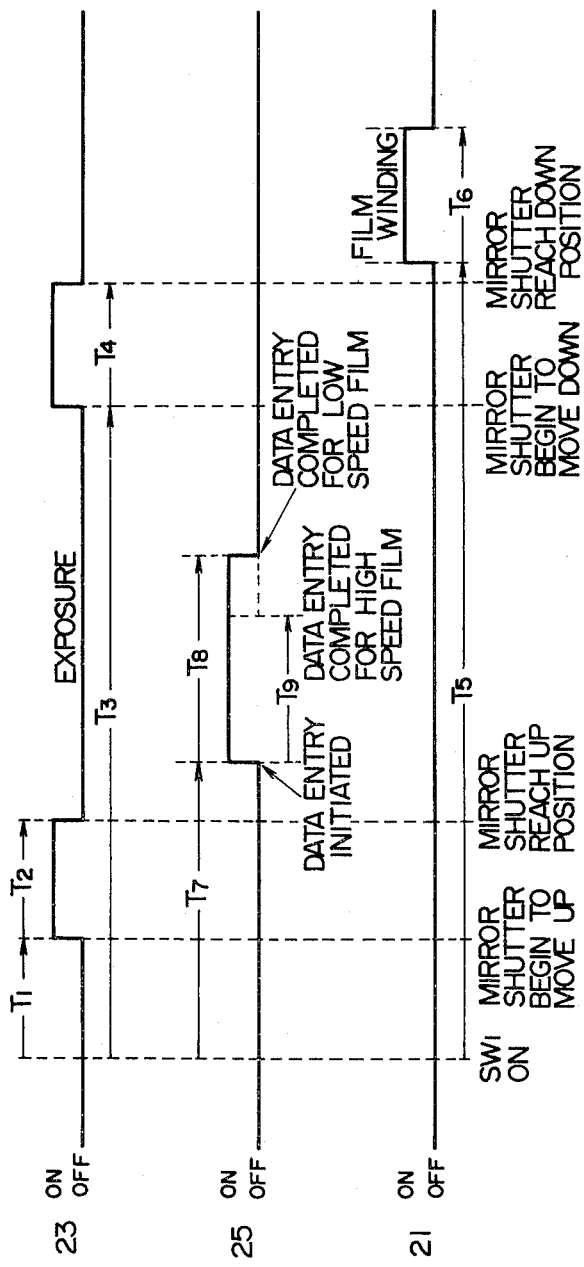
FIG. 12 is a timing chart which illustrates the operation of the camera apparatus of the invention.

It should be noted that timer circuits $TM_1$–$TM_9$ have individual time constants $T_1$–$T_9$ of different suitable values through a combination of suitable values for the capacitor $C_4$ and resistor $R_{12}$ (see FIG. 12).

Returning to FIG. 9, the detection and display means 27 and its associated control circuit 28 include portions 27B and 28B which are utilized to check the voltage of the internal battery 3. At this end, these portions are connected across a supply bus $E_3$, which is connected to the positive terminal of battery 3, and the common ground line $E_0$. The control circuit portion 28B comprises a comparator $CP_1$, a Zener diode $ZD_1$ which provides a constant voltage, three resistors $R_{15}$–$R_{17}$ and a manual switch $SW_3$. The switch $SW_3$ is connected in series with resistors $R_{15}$ and $R_{16}$ across the buses $E_3$ and $E_0$. The series combination of resistors $R_{15}$ and $R_{16}$ is shunted by a series circuit of resistor $R_7$ and Zener diode $ZD_1$ and also by comparator $CP_1$. Comparator $CP_1$ has its one input connected to the junction between resistors $R_{15}$ and $R_{16}$ and its other end connected to the junction between resistor $R_{17}$ and Zener diode $ZD_1$. The output of comparator $CP_1$ represents the output of the control circuit portion 28B, which is connected through a resistor $R_{18}$ to the cathode of light emitting diode 27B which represents detection and display means. Diode 27B has its anode connected to the bus $E_3$. These portions operate in response to the closure of the manual switch $SW_3$. Specifically, the supply voltage of the internal battery which is applied to the control circuit portion 28B through the switch $SW_3$ is divided by voltage divider resistors $R_{15}$ and $R_{16}$ and then applied to one input of the comparator $CP_1$. Zener diode $ZD_1$ provides a given voltage at its cathode which is applied to the other input of comparator $CP_1$, which then compares the supply voltage against the latter. When the applied voltage exceeds the given voltage, comparator $CP_1$ is turned on to cause an illumination of light emitting diode 27B, indicating that a supply voltage above the given value is available from the internal battery. If the supply voltage is less than the given voltage, comparator $CP_1$ remains off, whereby the failure of light emitting diode 27B to illuminate indicates that the internal battery 3 is exhausted.

Figure 10:
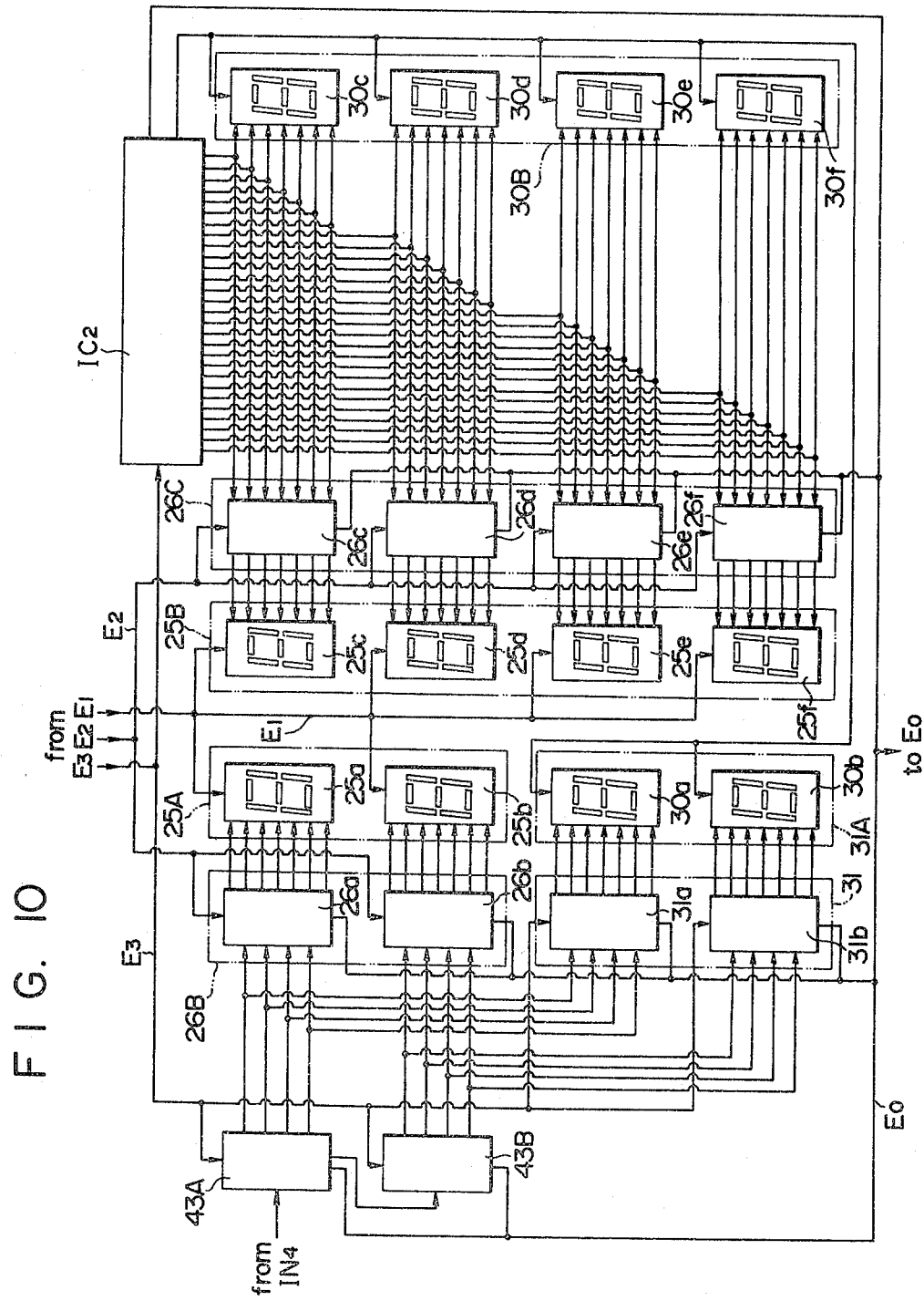
FIG. 10 is a circuit diagram of one form of the luminescent display shown in FIG. 9.

A detection circuit which detects the number of film frames is connected across the buses $E_3$ and $E_0$. It comprises a detecting switch $SW_4$, an inverter $IN_4$ which serves as a buffer to prevent a chattling of the switch $SW_4$, a capacitor $C_5$ and resistor $R_{19}$. The series circuit of resistor $R_{19}$ and capacitor $C_5$ as well as the inverter $IN_4$ are connected across the buses $E_3$ and $E_0$, and the capacitor $C_5$ is shunted by the switch $SW_4$. The inverter $IN_4$ has its input connected to the junction between the resistor $R_{19}$ and capacitor $C_5$, and its output is connected to the input of a first digit counter 43A which counts the number of frames, as shown in FIG. 10. The detection circuit detects marks such as perforations which are formed in the photographic film in order to permit a number of film frames to be detected. The detecting switch $SW_4$ is closed for each frame, and provides an input to the inverter $IN_4$. The input signal is shaped and inverted by the inverter $IN_4$, and is fed to the input of the counter 43A.

The luminescent display 42 shown in FIG. 9 is illustrated in more detail in FIG. 10. It includes the light emitting assembly 25 (25A, 25B) and its associated control circuit 26 (26A, 26B, 26C), the display 30 (30A, 30B) and its associated control circuit 31, a timing integrated circuit $IC_2$ which operates to produce the date when a picture is taken, and film frame counting counters 43A, 43B.

The light emitter assemblies 25A, 25B are formed by six light emitting elements 25a–25f such as light emitting diodes which are adapted to display numerals in seven segments. Each of the light emitting elements 25a–25f is connected to the bus $E_1$ through transistor $Q_3$ in the switching circuit 26A. The elements 25a–25f are driven by the external power supply 10 for illumination. Two of these elements, 25a, 25b, form light emitting assembly 25A which is used for entry of the number of film frames while the remaining four elements 25c–25f form together the light emitting element 25B which is used for entry of the photographing date. The elements 25a, 25b are connected to respective decoder drivers 26a, 26b through seven input lines which control the illumination of each of the seven segments. The decoder drivers 26a, 26b are connected to a first digit and a second digit counter 43A, 43B through four lines which transmit a single decimal digit. The first digit counter 43A has a carry signal line which is connected to the input of the second digit counter 43B. These counters 43A, 43B are connected across the buses $E_3$ and $E_0$, and thus is normally energized by the internal battery 3. The decoder drivers 26a, 26b are connected across the buses $E_2$ and $E_0$, and hence are rendered into operative condition upon application of a voltage thereto from the internal battery 3 whenever the camera apparatus 1 is mounted on the endoscope 2. The light emitting elements 25c–25f are connected to respective buffers 26c–26f through seven input lines which control the illumination of respective segments. The buffers 26c–26f are connected to the timing integrated circuit $IC_2$ through respective seven lines which are utilized to input a decode signal. The integrated circuit $IC_2$ is connected across the buses $E_3$ and $E_0$ and is hence normally fed from the internal battery 3 to continue counting the time. The buffers 26c–26f are connected across the buses $E_2$ and $E_0$, and hence are fed from the internal battery whenever the camera apparatus 1 is mounted on the endoscope 2. It is to be noted that the elements 25c, 25d represent the month while the elements 25e, 25f represent the day.

The display 30 (30A, 30B) is formed by six display elements 30a–30f, which represent liquid crystal elements, for displaying numerals in seven segments as is well known. Each of the display elements 30a–30f is connected to the bus $E_3$ through the timing integrated circuit $IC_2$, whereby it is normally fed from the internal battery 3 to provide an indication on the exterior of the camera apparatus 1. Two of these display elements, 30a, 30b, form the display unit 30A for indicating the number of film frames while the remaining four display elements 30c–30f form the display unit 30B which indicates the photographing date. The display elements 30a, 30b are connected to decoder drivers 31a, 31b through seven input lines which control the seven individual segments. These decoder drivers 31a, 31b are connected to the first digit and the second digit counter 43A, 43B through four lines which transmit a single decimal digit, these counters counting the number of film frames. The decoder drivers 31a, 31b are connected across the buses $E_3$ and $E_0$, and are normally fed from the internal battery 3. On the other hand, the display elements 30c–30f are directly connected to the timing integrated circuit $IC_2$ through seven input lines which control the seven segments, respectively. The display elements 30c, 30d represent the month while the display elements 30e, 30f represent the day.

The timing integrated circuit $IC_2$ is formed by a complementary metal-oxide-semiconductor large scale integrated circuit (CMOS-LSI) which is used for liquid crystal driver clock, and is connected across the supply lines $E_3$ and $E_0$, whereby it is normally fed from the internal battery 3 to effect the timing function and also driving the display elements 30c–30f.

The above description covers a specific form of an electrical circuit which is contained in the electrical control device 5 shown in FIG. 2. Referring to the timing chart shown in FIG. 12, the operation of the electrical control device 5 will be described briefly together with the operation of the camera apparatus 1.

Initially when the camera apparatus 1 is mounted on the endoscope 2, the detecting means 4 detects that the camera apparatus 1 is mounted, feeding the bus $E_2$ and the various circuits connected therewith from the internal battery 3. At the same time, the connection terminal 6 is brought into electrical contact with the output terminal 7 of the power supply, so that the bus $E_1$ as well as the various circuits connected therewith are fed from the external power supply 10, rendering the camera apparatus 1 to be capable of taking a picture.

When a shutter release button is depressed to close the shutter release switch $SW_1$, the resulting signal is shaped by the buffer 41 to be applied to respective timer circuits $TM_1$, $TM_3$, $TM_5$ and $TM_7$. In response to the signal applied, these timer circuits $TM_1$ to $TM_7$ are triggered, producing an "H" level output, causing a delay operation of these timer circuits to be initiated for respective intervals of $T_1$, $T_3$, $T_5$ and $T_7$. As indicated in FIG. 12, these time delays are chosen such that $T_1 < T_7 < T_3 < T_5$, so that after the time delay of $T_1$, timer circuit $TM_1$ is initially turned off, thus producing an "L" level output. In response to this output signal, the succeeding timer circuit $TM_2$ initiates to operate, producing an "H" level output for a time interval of $T_2$. This output signal is fed through OR circuit $OR_1$ to turn transistor $Q_1$ on. Thereupon, the electromagnet 23 is energized to cause the mirror shutter to bounce up, initiating an exposure of a film to an image from an object being photographed.

Then timer circuit $TM_7$ is turned off after the time delay of $T_7$, causing the succeeding timer circuits $TM_8$ and $TM_9$ to operate, which therefore produce output signals of an "H" level. If the film speed presetting switch $SW_2$ remains open at this time, the other input to AND circuit $AND_2$ will be "L" level while the other input to AND circuit $AND_3$ will be an "H" level, so that transistor $Q_4$ is turned on by AND circuit $AND_3$ for the time interval $T_9$ which is determined by timer circuit $TM_9$. If the switch $SW_2$ is closed, the other input to AND circuit $AND_2$ will be an "H" level while the other input to AND circuit $AND_3$ will be an "L" level, so that the transistor $Q_4$ will be turned on through AND circuit $AND_2$ for the time interval $T_8$ which is determined by timer circuit $TM_8$. When the transistor $Q_4$ is turned on, this also renders transistor $Q_3$ conductive, so that the light emitting assembly 25 is fed from the external power supply 10, causing the individual light emitting elements $25a$-$25f$ to emit light, allowing a digital entry onto the film to take place. The time interval determined by timer circuits $TM_8$ and $TM_9$ is determined so that $T_8 > T_9$, as indicated in FIG. 12, so that the data entry onto a film having a higher speed takes place when the switch $SW_2$ is opened while the data entry onto a film having a lower speed takes place when the switch is closed.

When timer circuit $TM_3$ is turned off after the time interval of $T_3$, the succeeding timer circuit $TM_4$ begins to operate, producing an output of an "H" level for the time interval of $T_4$. This output signal is fed through OR circuit $OR_1$ to turn transistor $Q_1$ on, whereby the electromagnet 23 is energized. This causes mirror shutter to move down into the taking light path from its upper position, whereby the exposure of the film to the image from an object being photographed is terminated.

Subsequently, timer circuit $TM_5$ is turned off after the time delay of $T_5$, whereby the succeeding timer circuit $TM_6$ begins to operate, producing an output of an "H" level for the time interval of $T_6$. This signal is fed through AND circuit $AND_1$ to turn transistor $Q_2$ on, whereby the motor 21 is fed from the external power supply 10. During the time interval of $T_6$, the motor 21 continues to be driven, effecting a film winding operation.

In this manner, a series of operations which are required to take a picture and including the upward movement of the mirror shutter, the exposure of the film, the data entry, the downward movement of the mirror shutter and the film winding operation are electrically controlled in an automatic manner.

It should be noted that the electrical circuit of the electrical control device shown in FIGS. 9 to 11 can be directly applied to the camera apparatus 41 of FIGS. 3 and 4 and to the camera apparatus 51 of FIGS. 7 and 8, by slightly modifying the connection of the bus $E_1$ with the power supply. Specifically, when it is applied to the camera apparatus 41, the bus $E_1$ is connected through the detecting means 4 to the internal battery 3. In the case of the camera apparatus 51, the bus $E_1$ may be connected through the relay circuit 54, acting as detecting means, to the connection terminal 6. In this manner, a desired function for the electrical circuit of the electrical control device can be obtained.

While in the described embodiments, the detecting means comprises a pair of detection terminals and a conductive member, a combination of light emitting and light receiving element or a relay circuit, any other conventional means such as microswitch or pressure-sensitive element may be used instead.

It should be understood that the electrical circuits shown in FIGS. 9 to 11 are exemplary only, and that the invention is not limited to the electrical circuit shown or any other circuit similar thereto.

What is claimed is:

1. A camera apparatus adapted to be mounted on an endoscope, said apparatus comprising:
    a first electrical circuit located in said camera which must be energized both during a photographing operation and when no photographing operation is in progress;
    a second electrical circuit located in said camera which must be energized during said photographing operation;
    a battery located in said camera for energizing at least said first electrical circuit;
    a connection terminal located on said camera and adapted to be connected to an external power supply associated with the endoscope when said camera is connected to the endoscope; and
    detecting means for detecting whether said camera apparatus if mounted on an endoscope, said detecting means connecting said connection terminal to said second electrical circuit during said photographing operation when said camera apparatus is mounted on the endoscope.

2. A camera apparatus adapted to be mounted on an endoscope, said apparatus comprising:
    a first electrical circuit located in said camera which must be energized both during a photographing operating and when no photographing operation is in progress;
    a second electrical circuit located in said camera which must be energized during said photographing operation;
    a battery located in said camera for energizing at least said first electrical circuit; and
    detecting means for detecting whether said camera apparatus is mounted on an endoscope, said detecting means being for connecting said second electrical circuit to said battery during a photographing operation when said camera apparatus is mounted on the endoscope.

3. A camera apparatus according to claim 1 or 2, in which said detecting means further comprises:
 a conductive member adapted to be disposed on an eyepiece assembly of an endoscope; and
 a pair of detecting terminals adapted to contact said conductive member simultaneously as said camera apparatus is mounted on an eyepiece assembly of the endoscope.

4. A camera apparatus according to claim 1 or 2, in which said detecting means comprises:
 a light receiving element;
 a light emitting element adapted to be disposed in the eyepiece assembly of an endoscope in such a manner as to be located opposite and aligned with said light receiving element when said camera apparatus is mounted on an eyepiece assembly of the endoscope;
 a retractable light shield member for preventing said light receiving element from receiving light when said camera apparatus is not mounted on the eyepiece of an endoscope; and
 means for retracting said light shield member as said camera apparatus is mounted on the endoscope, for allowing said light receiving element to receive light from said light emitting element.

5. A camera apparatus according to claim 1, in which said detecting means comprises a switch circuit for electrically connecting said connection terminal to the external power supply when said camera apparatus is mounted on an eyepiece assembly of the endoscope.

6. A camera apparatus according to claim 1 in which said detecting means is for connecting said second electrical circuit to a power supply of a light source unit of an endoscope.

7. A camera apparatus according to claim 1 or 2, in which said second electrical circuit further comprises:
 a motor for winding film;
 an electromagnet for controlling the operation of a mirror shutter;
 a light emitting element for forming a data entry on a film; and
 detection and display means for detecting and displaying one of a film speed and the voltage of said internal battery.

* * * * *